United States Patent
Hub et al.

(10) Patent No.: US 6,232,513 B1
(45) Date of Patent: May 15, 2001

(54) ISOMERIZATION OF HYDROFLUOROCARBON

(75) Inventors: Serge Hub, Villeurbanne; Dominique Guillet, Vernaison, both of (FR)

(73) Assignee: Elf Atochem S.A., Paris (FR)

( * ) Notice: Subject to any disclaimer, the term of this patent is extended or adjusted under 35 U.S.C. 154(b) by 0 days.

(21) Appl. No.: 09/341,760

(22) PCT Filed: Jan. 9, 1998

(86) PCT No.: PCT/FR98/00035

§ 371 Date: Dec. 22, 1999

§ 102(e) Date: Dec. 22, 1999

(87) PCT Pub. No.: WO98/31650

PCT Pub. Date: Jul. 23, 1998

(30) Foreign Application Priority Data

Jan. 17, 1997 (FR) .................................................. 9700477

(51) Int. Cl.$^7$ .................................................. C07C 19/08
(52) U.S. Cl. .................................................. 570/151
(58) Field of Search ............................... 570/151

(56) References Cited

U.S. PATENT DOCUMENTS

| 2,315,871 | | 4/1943 | Oberfell et al. . |
| 4,902,838 | | 2/1990 | Manzer et al. . |
| 4,950,815 | | 8/1990 | Moore et al. . |
| 5,030,372 | * | 7/1991 | Manogue et al. ............... 570/151 |
| 5,091,600 | | 2/1992 | Moore et al. . |

FOREIGN PATENT DOCUMENTS

| 2-115135 | 4/1990 | (JP) . |
| 365296 | 4/1990 | (EP) . |
| 3-261731 | 11/1991 | (JP) . |
| WO 95/15300 | 6/1995 | (WO) . |

* cited by examiner

*Primary Examiner*—Alan Siegel
(74) *Attorney, Agent, or Firm*—Smith, Gambrell & Russell

(57) ABSTRACT

In order to isomerize a hydrofluorocarbon having a certain thermodynamic stability (HFC 1) into a hydrofluorocarbon of greater thermodynamic stability (HFC 2), the hydrofluorocarbon HFC 1 is subjected to a heat treatment in the presence of hydrogen at a temperature above 500° C.

This process, which does not require the use of a catalyst, applies especially to the isomerization of 1,1,2,2-tetrafluoroethane into 1,1,1,2-tetrafluoroethane.

9 Claims, No Drawings

ISOMERIZATION OF HYDROFLUOROCARBON

This application is a 371 of PCT/FR98/00035 filed Jan. 9, 1998.

FIELD OF THE INVENTION

The subject of the present invention, which relates to the field of fluorinated hydrocarbons, is the isomerization of hydrofluorocarbons (HFC) and, more particularly, that of 1,1,2,2-tetrafluoroethane (F134) into 1,1,1,2-tetrafluoroethane (F134a).

BACKGROUND OF THE INVENTION

F134a is one of the hydrofluorocarbons (HFC) falling within the context of the replacement of the chlorofluorocarbons (CFC) and hydrochlorofluorocarbons (HCFC) which have already been banned or are in the process of being banned because of their harmful effect on the stratospheric ozone layer.

Several ways of obtaining F134a are known, namely:
- the fluorination of 1-chloro-2,2,2-tri-fluoroethane (F133a) in gas or liquid phase;
- the fluorination of trichloroethylene in liquid phase;
- the hydrogenolysis of 1,1-dichloro-1,2,2,2-tetrafluoroethane (F114a) or of 1-chloro-1,2,2,2-tetrafluoroethane (F124);
- the isomerization of 1,1,2,2-tetrafluoroethane (F134).

According to the literature, the latter process is carried out using catalysts. Thus, Patents EP 365,296 and JP 03 261731 describe the use of chromium-based catalysts and U.S. Pat. No. 4,902,838 claims a catalyst of the fluorinated alumina type; Patent JP 02 115135 prefers to use a catalyst of the aluminium chlorofluoride type. The use of a catalyst is not always sufficient; thus, U.S. Pat. No. 4,902,838 recommends introducing oxygen into the medium so as to maintain the catalytic activity over time and Patent Application WO 95/15300 recommends introducing a source of chloride ions.

DESCRIPTION OF THE INVENTION

It has now been found that it is possible to isomerize F134 into F134a without the aid of a catalyst, by a simple heat treatment in the presence of hydrogen. This method may also apply to the isomerization of other HFCs, for example to that of 1,1,2-trifluoroethane (F143) into 1,1,1-trifluoroethane (F143a) or to that of 1,2-difluoroethane (F152) into 1,1-difluoroethane (F152a).

The subject of the present invention is therefore a process for the isomerization of a hydrofluorocarbon having a certain thermodynamic stability (HFC 1) into a hydrofluorocarbon of greater thermodynamic stability (HFC 2), characterized in that the hydrofluorocarbon HFC 1 is subjected to a heat treatment in the presence of hydrogen at a temperature above 500° C.

The process according to the invention is advantageously carried out at a temperature of between 500 and 1000° C., preferably between 600 and 750° C.

The pressure of the reaction may be between 0.1 and 50 bar, but it is preferred to work between atmospheric pressure and 20 bar.

The $H_2$/HFC 1 molar ratio may range from 1 to 100, but it is generally preferred to work with a molar ratio of between 2 and 20. The flux of reactants (HFC 1 and $H_2$) entering the reactor may be diluted with an inert gas, such as helium or nitrogen.

The residence time of the reactants in the hot part of the reactor may vary over wide ranges. It varies inversely with the temperature and is generally between 0.1 and 1000 seconds, preferably between 1 and 300 seconds.

The isomerization may be carried out in an empty reactor, i.e. a reactor which contains no packing but which may, however, be equipped with thermocouples and baffles. The reactor may be made of quartz or metal. In this case, the metal of the material forming the reactor may be chosen from metals such as nickel, iron, titanium, chromium, molybdenum, cobalt and gold, or their alloys. The metal, chosen more particularly for limiting the corrosion or the catalytic phenomena, may form a solid wall or it may be plated onto another metal, as in the case of a reactor gold-plated on its internal surface.

EXAMPLES

The following examples illustrate the invention without limiting it.

Examples 1 to 3

Trials were carried out at atmospheric pressure in a quartz tube reactor, having a length of 47 cm and an internal diameter of 2.1 cm, placed in an electric furnace having a power of 1.5 kW; the temperature of the furnace was measured using a thermocouple.

The reactants (F134 and $H_2$) were introduced simultaneously via mass flow meters allowing the flow rates, and therefore the molar ratios, to be controlled.

The gaseous products were analysed by in-line chromatography (GC) at the outlet of the reactor.

The following table summarizes the operating conditions and the results obtained.

| EXAMPLE | 1 | 2 | 3 |
|---|---|---|---|
| Operating conditions: | | | |
| temperature (° C.) | 700 | 700 | 700 |
| $H_2$ flow rate (mmol/h) | 509 | 187.1 | 29.9 |
| F134 flow rate (mmol/h) | 50.4 | 96 | 31.7 |
| residence time (s) | 10 | 21 | 95 |
| Results: | | | |
| conversion of F134 | 23% | 27% | 47% |
| F134a selectivity | 81% | 82% | 81% |

Examples 4 to 6

Trials were carried out at atmospheric pressure in a quartz tube reactor, having a length of 47 cm and an internal diameter of 1.5 cm, placed in an electric furnace having a power of 1.5 kW; the temperature of the furnace was measured using a thermocouple.

The following table summarizes the operating conditions and the results obtained:

| EXAMPLE | 4 | 5 | 6 |
|---|---|---|---|
| Operating conditions: | | | |
| temperature (° C.) | 700 | 700 | 700 |
| $H_2$ flow rate (mmol/h) | 301.3 | 141.5 | 59.8 |

-continued

| EXAMPLE | 4 | 5 | 6 |
|---|---|---|---|
| F134 flow rate (mmol/h) | 15.2 | 15.2 | 15.2 |
| residence time (s) | 4.9 | 9.9 | 20.6 |
| Results: | | | |
| conversion of F134 | 13% | 24% | 38% |
| F134a selectivity | 84% | 78% | 79% |

Example 7

The operation was carried out as in Examples 1 to 3, but by replacing the quartz reactor with a reactor made of Inconel 600 of the same size. By working under the following operating conditions:

| | |
|---|---|
| temperature | 700° C. |
| H₂ flow rate | 29.9 mmol/h |
| F134 flow rate | 31.7 mmol/h |
| residence time | 95 seconds | a conversion of F134 of 44% and an F134a selectivity of 74% were obtained.

Comparative Examples 8 and 9

The operation was carried out in the same way as in Examples 1 to 3, but by replacing the hydrogen with helium. The following table summarizes the operating conditions and the results obtained:

| EXAMPLE | 8 | 9 |
|---|---|---|
| Operating conditions: | | |
| temperature (° C.) | 700 | 700 |
| He flow rate (mmol/h) | 312.1 | 35.3 |
| F134 flow rate (mmol/h) | 22.3 | 31.7 |
| residence time (s) | 18 | 95 |

-continued

| EXAMPLE | 8 | 9 |
|---|---|---|
| Results: | | |
| conversion of F134 | 3% | 15% |
| F134a selectivity | 33% | 60% |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Process comprising isomerization of a hydrofluorocarbon having a certain thermodynamic stability (HFC 1) into a hydrofluorocarbon of greater thermodynamic stability (HFC 2), the hydrofluorocabon (HFC 1) is heat treated in the presence of hydrogen at a temperature above 500° C.

2. Process according to claim 1, in which the reaction is carried out at a temperature of between 500 and 1000° C.

3. Process according to claim 1, wherein the reaction is carried out at a pressure of between 0.1 and 50 bar.

4. Process according to claim 1, wherein the hydrogen/hydrofluorocarbon (HFC 1) molar ratio is between 1 and 100.

5. Process according to claim 1, wherein the reaction is carried out in an empty reactor made of metal or quartz.

6. Process according to claim 1, wherein the hydrofluorocarbon to be isomerized (HFC 1) is 1,1,2,2-tetrafluoroethane.

7. Process according to claim 2, wherein the temperature is between 600 and 750° C.

8. Process according to claim 3, wherein the pressure is from atmospheric up to 20 bar.

9. Process according to claim 4, wherein the molar ratio is between 2 and 20.

* * * * *